(12) United States Patent
Dertinger et al.

(10) Patent No.: US 11,016,101 B2
(45) Date of Patent: *May 25, 2021

(54) SIMPLIFIED NUCLEI ANALYSIS PLATFORM AND BIOMARKER MATRIX THAT SUPPORTS GENOTOXIC MODE OF ACTION DETERMINATIONS

(71) Applicant: Litron Laboratories, Ltd., Rochester, NY (US)

(72) Inventors: Stephen D. Dertinger, Webster, NY (US); Steven M. Bryce, Rochester, NY (US); Jeffrey C. Bemis, Rochester, NY (US)

(73) Assignee: LITRON LABORATORIES LTD., Rochester, NY (US)

( * ) Notice: Subject to any disclaimer, the term of this patent is extended or adjusted under 35 U.S.C. 154(b) by 111 days.

This patent is subject to a terminal disclaimer.

(21) Appl. No.: 16/176,237

(22) Filed: Oct. 31, 2018

(65) Prior Publication Data

US 2019/0064150 A1 Feb. 28, 2019

Related U.S. Application Data

(60) Continuation of application No. 15/836,624, filed on Dec. 8, 2017, now Pat. No. 10,802,013, which is a continuation of application No. 15/263,291, filed on Sep. 12, 2016, now Pat. No. 9,857,358, which is a division of application No. 14/201,138, filed on Mar. 7, 2014, now Pat. No. 9,470,694.

(60) Provisional application No. 61/775,494, filed on Mar. 9, 2013.

(51) Int. Cl.
| | |
|---|---|
| *G01N 33/533* | (2006.01) |
| *G01N 33/68* | (2006.01) |
| *G01N 33/50* | (2006.01) |
| *G01N 1/30* | (2006.01) |

(52) U.S. Cl.
CPC ....... *G01N 33/6875* (2013.01); *G01N 33/502* (2013.01); *G01N 33/5014* (2013.01); *G01N 33/5044* (2013.01); *G01N 33/5076* (2013.01); *G01N 33/533* (2013.01); *G01N 33/6878* (2013.01); *G01N 1/30* (2013.01)

(58) Field of Classification Search
CPC ............. G01N 33/5014; G01N 33/502; G01N 33/5011; G01N 33/5076; G01N 33/533; G01N 33/6875; G01N 33/6878
See application file for complete search history.

(56) References Cited

U.S. PATENT DOCUMENTS

| | | | |
|---|---|---|---|
| 7,445,910 B2 * | 11/2008 | Dertinger | G01N 1/30 |
| | | | 435/40.5 |
| 9,470,694 B2 | 10/2016 | Dertinger et al. | |
| 9,857,358 B2 | 1/2018 | Dertinger et al. | |
| 2003/0134305 A1 | 7/2003 | Dertinger et al. | |
| 2005/0026197 A1 | 2/2005 | Dertinger | |
| 2006/0040291 A1 | 2/2006 | Dertinger et al. | |
| 2007/0274919 A1 | 11/2007 | Dertinger | |
| 2008/0311586 A1 | 12/2008 | Dertinger et al. | |
| 2009/0311706 A1 | 12/2009 | Dertinger | |
| 2010/0112594 A1 | 5/2010 | Dertinger et al. | |
| 2012/0129160 A1 | 5/2012 | Dertinger et al. | |
| 2013/0177921 A1 * | 7/2013 | Chastain | C12Q 1/68 |
| | | | 435/6.19 |
| 2014/0017673 A1 | 1/2014 | Dertinger et al. | |
| 2015/0140123 A1 | 5/2015 | Mueller et al. | |
| 2018/0100851 A1 * | 4/2018 | Dertinger | G01N 33/5076 |

FOREIGN PATENT DOCUMENTS

WO 2011/150023 A1 12/2011

OTHER PUBLICATIONS

Muslimovic et al. An optimized method for measurement of gamma-H2AX in blood mononuclear and cultured cell. Nature Protocols. 3 (7): 1187-1193 (2008).*
Yang et al. AZD1152, a novel and selective aurora B kinase inhibitor, induces growth arrest, apoptosis, and sensitization for tubulin depolymerizing agent or topoisomerase II inhibitor in human acute leukemia cells in vitro and in vivo. Blood 110 (6): 2034-2040 (Sep. 15, 2007).*
Smart et al., "Genotoxicity Screening via the (Gamma)H2AX by Flow Assay," Mut. Res. 715:25-31 (2011).
International Search Report and Written Opinion for corresponding Patent Application No. PCT/US2014/021837 (dated Aug. 12, 2014).
Muslimovic et al., "An Optimized Method for Measurement of Gamma-H2AX in Blood Mononuclear and Cultured Cells," Nat. Prot. 3(7):1187-1193 (2008).
Schreiber et al., "Multiparametric Flow Cytometric Analysis of Radiation-Induced Micronuclei in Mammalian Cell Cultures," Cytometry 13:90-102 (1992).
Bryce et al., "Miniaturized Flow Cytometric In Vitro Micronucleus Assay Represents an Efficient Tool for Comprehensively Characterizing Genotoxicity Dose-Response Relationships," Mutat. Res. 703(2):191-199 (2010).
Yang et al., "AZD1152, A Novel and Selective Aurora B Kinase Inhibitor, Induces Growth Arrest, Apoptosis, and Sensitization for Tubulin Depolymerizing Agent or Topoisomerase II Inhibitor in Human Acute Leukemia Cells In Vitro and In Vivo," Blood 110(6):2034-2040 (2007).

(Continued)

*Primary Examiner* — Gailene Gabel
(74) *Attorney, Agent, or Firm* — Troutman Pepper Hamilton Sanders LLP (Rochester)

(57) ABSTRACT

The present invention relates a simple method for evaluating free eukaryotic cell nuclei for biomarkers of DNA damage and/or transcription factor activation, activity, or expression levels and/or epigenetic modifications to chromatin or chromatin-associated factors. The invention also teaches useful strategies for combining nuclear biomarkers into a matrix of endpoints that are capable of elucidating genotoxicants' primary mode of DNA-damaging activity. Kits for conducting methods according to the invention are also described.

20 Claims, 3 Drawing Sheets

(56) References Cited

OTHER PUBLICATIONS

Bradbury et al., "Measurement of the ADP:ATP Ratio in Human Leukaemic Cell Lines can be Used as an Indicator of Cell Viability, Necrosis and Apoptosis," J. Immunol. Methods 240:79-92 (2000).
Rosner et al., "Merging High-Quality Biochemical Fractionation with a Refined Flow Cytometry Approach to Monitor Nucleocytoplasmic Protein Expression Throughout the Unperturbed Mammalian Cell Cycle," Nat. Protocols 8 (3):602-626 (2013).
Parry et al., "Detection and Characterization of Mechanisms of Action of Aneugenic Chemicals," Mutagenesis 17 (6):509-521 (2002).
Extended Search Report for EP14779502.5 dated Aug. 12, 2016.
Office Action dated Sep. 17, 2015 for U.S. Appl. No. 14/201,138.
Office Action dated Nov. 17, 2016 for U.S. Appl. No. 15/263,291.
Office Action dated Sep. 7, 2018 for U.S. Appl. No. 15/836,624.
Office Action for U.S. Appl. No. 15/836,624, dated Dec. 27, 2019.
Examination Report in European Patent Application No. 14779502.5 dated Mar. 31, 2020.
Restriction Requirement in U.S. Appl. No. 14/201,138 dated Jun. 12, 2015.
Office Action in U.S. Appl. No. 15/836,624 dated Jan. 26, 2018.
Office Action in U.S. Appl. No. 15/836,624 dated Apr. 4, 2019.
Examination Report in European Patent Application No. 14779502.5 dated May 29, 2019.
Examination Report in European Patent Application No. 14779502.5 dated Mar. 25, 2021.

\* cited by examiner

SIMPLIFIED NUCLEI ANALYSIS PLATFORM AND BIOMARKER MATRIX THAT SUPPORTS GENOTOXIC MODE OF ACTION DETERMINATIONS

This application is a continuation of U.S. patent application Ser. No. 15/836,624, filed Dec. 8, 2017, now U.S. Pat. No. 10,802,013, issued Oct. 13, 2020, which is a continuation of U.S. patent application Ser. No. 15/263,291, filed Sep. 12, 2016, now U.S. Pat. No. 9,857,358, which is a divisional of U.S. patent application Ser. No. 14/201,138, filed Mar. 7, 2014, now U.S. Pat. No. 9,470,694, which claims the priority benefit of U.S. Provisional Patent Application Ser. No. 61/775,494, filed Mar. 9, 2013, which are hereby incorporated by reference in their entirety.

FIELD OF THE INVENTION

This invention relates to a simple method for evaluating free eukaryotic cell nuclei for biomarkers of DNA damage and/or transcription factor activation, activity, or expression levels and/or epigenetic modifications to chromatin or chromatin-associated structures. The invention also teaches useful strategies for combining nuclear biomarkers into a matrix that is capable of determining genotoxicants' primary mode of DNA-damaging activity.

BACKGROUND OF THE INVENTION

The cell nucleus is a membrane-bound organelle found in eukaryotic cells. The nucleus houses the majority of each cell's nucleic acid content, and is therefore considered the control center that directs gene expression and protein synthesis. The long, linear, double-helix DNA molecules are ordinarily maintained in structures called chromosomes, and histones as well as other chromatin-associated structures are known to play an important role in maintaining this higher order configuration.

Nuclei and the processes that they govern are of extreme importance to biological sciences. Methods for analyzing nuclei and the function of the nucleic acids they contain are extremely diverse, and include stable transfection, gene knock-out and knock-in techniques, western blotting, site-directed mutagenesis, DNA sequencing, electron microscopy, image analysis, and polymerase chain reaction (PCR). The list continues to grow given the importance of cells' genetic material. Indeed, many lines of investigation benefit from an understanding of how cells and nuclei in particular react to certain stimuli. For instance, biomarkers of DNA damage can be useful for determining whether a test chemical is DNA-reactive and therefore likely to be mutagenic. Nuclei are especially well suited to make these assessments since they house the bulk of cells' genetic material, and numerous DNA damage-responsive pathways within this organelle have been described.

Responses to DNA damage typically involve soluble protein factors that reside within the cytosol and/or the nucleus. Upon DNA damage, some are activated via phosphorylation, some become translocated from cytosol to nucleus, and others are controlled in other manners, for instance cleavage which activates an enzymatic function. These types of responses can be studied with antibodies or other high affinity reagents that specifically recognize altered DNA and/or proteins that have been translocated to the nucleus, activated, or otherwise modified to deal with the damage. The literature is full of techniques that are capable of studying these types of activities, and include western blotting, cleavage of luminescent substrates, electrophoretic mobility shift assays, image analysis, and flow cytometry, among others. Image analysis and other visual assessments based on microscopy tend to call for cell fixation, antibody labeling, and washing steps. Similarly, flow cytometric approaches tend to specify several processing steps whereby antibodies specific for DNA damage or proteins associated with damage are applied to fixed cells or liberated nuclei, followed by removal of unbound fluorescent reagents via a centrifugation or similar steps. For many types of analyses, heat and/or other strong denaturing conditions are applied to provide the antibody(s) with greater access to nuclei-associated epitopes. For many laboratory environments, especially where higher throughput is required, it would be preferable to utilize a so-called "homogeneous assay" whereby cells are simply brought into contact with one solution and then analyzed without the need for further sample processing steps.

The present invention overcomes the disadvantages of prior art approaches, and satisfies the need of establishing robust, reliable, high throughput methods for evaluating nuclei for biomarkers of DNA damage and/or transcription factor activation, activity, or expression levels and/or epigenetic modifications to chromatin or chromatin-associated factors.

SUMMARY OF THE INVENTION

As used herein, the terms "nuclei", "nuclei events", "detergent-liberated nuclei", and "free nuclei" are used interchangeably to describe chromatin and other nuclear factors that are surrounded by a nuclear membrane and that have been liberated from cells through contact with one or more cell lysis (e.g., detergent-containing) solutions.

As used herein, these terms, "nuclei", etc., are also inclusive of bundles of metaphase chromosomes that lack a nuclear envelop but none-the-less remain together in an aggregated state upon contact with the one or more cell lysis solutions. Importantly, the aggregation is not excessive whereby multiple cells' metaphase chromosomes are found to clump together, rather these bundles of metaphase chromosomes remain in units that correspond to single cells' metaphase chromosomes. Without being bound by belief, it is believed that the most likely explanation for this advantageous state of aggregation is that upon digestion of cytoplasmic membranes, cytosolic and/or metaphase-associated fibers envelop the metaphase chromosomes, resulting in maintenance of their chromosome complement.

As used herein, the term "chromatin debris" is used to describe chromatin that is associated with dead and/or dying cells. In these instances, the chromatin may or may not be bound by a nuclear envelope, and the chromatin may or may not exist in typical amounts. For instance, apoptotic bodies will generally have sub-2n DNA content owing to the fragmentation of nuclei that occurs during this process of cell death. None-the-less, there are some applications of the current invention that would benefit from analysis of these particles for nuclei-associated epitopes, and in these cases the term "chromatin debris" is used.

As used herein, "NAESA/L" refers to fluorescent nuclei-associated epitope-specific antibody or other high affinity ligand, including antibody fragments that retain binding specificity to the nuclei-associated epitope of interest, as well as polypeptide antibody mimics or nucleic acid aptamers that exhibit binding specificity for the nuclei-associated epitope of interest.

A first aspect of the invention relates to a method for analyzing detergent-liberated nuclei and/or chromatin debris for nuclei-associated epitopes. The method includes: contacting a sample containing eukaryotic cells with a solution comprising one or more cell lysis reagents, a fluorescent nucleic acid dye (NAD), and one or more NAESA/L, the NAD and one or more NAESA/L having distinct fluorescent emission spectra, said contacting being effective to digest eukaryotic cell cytoplasmic membranes but not nuclear membranes, aggregate metaphase chromosomes of a single cell into a single bundle of chromosomes, label chromatin with the NAD, and label the one or more nuclei-associated epitopes with the one or more NAESA/L; exciting the NAD and one or more NAESA/L with light of an appropriate excitation wavelength; detecting fluorescent emission and light scatter produced by the nuclei and/or chromatin debris and counting one or more of the following events: the number of nuclei, the number of nuclei positively labeled by the one or more NAESA/L, the number of chromatin debris, the number of chromatin debris positively labeled by the one or more NAESA/L, the number of nuclei in G1, S, and G2/M phases of the cell cycle, and the number of polyploid nuclei; and determining one or more of the following measurements: the frequency of nuclei positively labeled by the one or more NAESA/L relative to total nuclei, the frequency of chromatin debris positively labeled by the one or more NAESA/L relative to total chromatin debris and/or total nuclei, the proportion of nuclei in G1, S, and G2/M phases of the cell cycle, the proportion of polyploid nuclei, and mean and/or median fluorescence of the one or more NAESA/L.

A second aspect of the present invention relates to a method for assessing the response of nuclei-associated biomarkers of DNA damage and/or transcription factor activation, activity, or expression levels and/or epigenetic modifications resulting from a chemical or physical agent. This method includes: exposing eukaryotic cells, previously exposed to a chemical or physical agent, to a solution comprising one or more cell lysis reagents, optionally RNase, a NAD, and one or more NAESA/L, the NAD and one or more NAESA/L having distinct fluorescent emission spectra, said exposing being effective to digest eukaryotic cell cytoplasmic membranes but not nuclear membranes, aggregate metaphase chromosomes of a single cell into a single bundle of chromosomes, label chromatin with the NAD, and label the one or more nuclei-associated epitopes with the one or more NAESA/L; exciting the NAD and one or more NAESA/L with light of an appropriate excitation wavelength; detecting fluorescent emission and light scatter produced by the nuclei and/or chromatin debris and counting one or more of the following events: the number of nuclei, the number of NAESA/L-positive nuclei, the number of chromatin debris, the number of NAESA/L-positive chromatin debris, the number of nuclei in G1, S, and G2/M phases of the cell cycle, and the number of polyploid nuclei. Changes to the proportion of NAESA/L-positive nuclei relative to total nuclei and/or changes to the proportion of NAESA/L-positive chromatin debris relative to total chromatin debris and/or total nuclei indicates that the chemical or physical agent affected the nuclear biomarker. Another valuable endpoint that is relevant for some nuclei biomarkers is a measure of central tendency of NAESA/L-associated fluorescence. In the context of assessing a chemical or physical agent, the change (i.e., the "shift") in mean and/or median fluorescence of the one or more NAESA/L for an exposed sample, compared to unexposed or negative control eukaryotic cells, indicates that the chemical or physical agent affected the nuclear biomarker.

A third aspect of the present invention relates to a method of assessing the toxicity of a chemical or physical agent. The method includes: exposing eukaryotic cells to a chemical or physical agent and performing the method according to the first aspect of the invention wherein, in comparison to unexposed or negative control eukaryotic cells, a significant change to the proportion of the one or more NAESA/L-positive nuclei relative to total nuclei and/or change to the proportion of the one or more NAESA/L-positive chromatin debris relative to total chromatin debris and/or total nuclei indicates that the chemical or physical agent affected the nuclei-associated epitope of interest; a significant change to the proportion of nuclei in one or more phases of the cell cycle and/or in the proportion of polyploid nuclei indicates that the chemical or physical agent perturbed the cell cycle; and a significant change in the one or more NAESA/L-positive nuclei and/or chromatin debris indicate that the chemical or physical agent affected the nuclei-associated epitope of interest, whereby an effect of the chemical or physical agent on two or more of these endpoints allows a determination of the type of toxicity caused by the chemical or physical agent.

In accordance with these aspects, and without limitation thereto, in certain embodiments the one or more endpoints may include one or more of an increase in the phosphorylated histone 2AX ($\gamma$H2AX), which indicates clastogenic activity; an increase in the phosphorylated histone 3 (H3) or polyploidy nuclei, each of which indicates aneugenic activity; an increase in cleaved poly(ADP-ribose) polymerase (PARP)+ events, cleaved caspase 3 (Cas 3)+ events, cleaved caspase 7 (Cas 7)+ events, cleaved caspase 9 (Cas 9)+ events, tetramethylrhodamine ethyl ester (TMRE)-events, ethidium monoazide bromide (EMA)+, or propidium monoazide bromide (PMA)+ events indicates cytotoxicity; and a reduction in nuclei to bead ratios or nuclei to time ratios, or ATP levels indicates cytotoxicity.

A fourth aspect of the present invention is related to a panel of NAESA/Ls that can be used singularly or in combination to achieve several measurements that are valuable for discriminating genotoxic agents' primary mode of action. In performing the method according to the first, second, or third aspects of the invention using a singular NAESA/L, then additional NAESA/Ls can be used in parallel to assess other epitopes. Alternatively, multiple compatible NAESA/L can be used in a single sample for simultaneous measurement of NAESA/L biomarkers. The NAD and NAESA/L are excited with light of appropriate excitation wavelength(s), and any one or more, preferably two or more, of above-identified events or changes in proportions are determined. A shift in an exposed sample's NAESA/L-associated fluorescence compared to unexposed or negative control eukaryotic cells may also be used to indicate that the chemical or physical agent affected the nuclear biomarker. By considering the effect of chemical or physical agent treatment on the two or more of these endpoints, a determination of genotoxic MOA is made, and discriminated from cytotoxic activity.

A fifth aspect of the present invention relates to a kit that includes one or more eukaryotic cell membrane lysis solutions; a NAD; and one or more NAESA/L that bind specifically to a nuclei-associated epitope, preferably two or more NAESA/L that bind specifically to two or more distinct nuclei-associated epitopes. The kit may optionally contain one or more additional components and reagents, including a third NAESA/L that binds specifically to a third epitope associated with cytotoxicity; a reagent that is responsive to cytotoxicity (e.g., a reagent that labels a marker of mitochondrial health, for instance a mitochondrial membrane potential dye, or is a dye that is otherwise responsive to cytotoxicity); RNase; counting beads; and a computer-readable medium that contains instructions for statistical analyses for characterizing in vitro genotoxicity as the result of clastogenicity, aneugenicity, or cytotoxicity based on the behavior of a eukaryotic cell in response to exposure to a chemical or physical agent and following exposure to the kit components. The kit may further include instructions for use of the kit components. In certain embodiments, the one or more eukaryotic cell membrane lysis solutions also contain(s) all other reagents supplied with the kit.

A sixth aspect of the invention relates to a kit that includes one or more eukaryotic cell membrane lysis solutions; RNase, a NAD, a computer-readable medium that contains instructions for statistical analyses for characterizing toxicity as the result of clastogenicity, aneugenicity, or cytotoxicity based on the behavior of a eukaryotic cell in response to in vitro exposure to a chemical or physical agent and following exposure to the kit components with one or more NAESA/L that bind specifically to one or more nuclei-associated epitopes, preferably two or more NAESA/L that bind specifically to two or more distinct nuclei-associated epitopes as described above, and optionally a third NAESA/L that binds specifically to a third epitope associated with cytotoxicity or a reagent that is responsive to cytotoxicity (e.g., a reagent that labels a marker of mitochondrial health, for instance a mitochondrial membrane-potential dye or luminescent ATP-specific reagent, or is a reagent that is otherwise responsive to cytotoxicity). The kit may further include instructions for use of the kit components. In certain embodiments, the one or more eukaryotic cell membrane lysis solutions also contain(s) all other reagents supplied with the kit.

A seventh aspect of the invention relates to a reagent for performing the methods of the present invention. The reagent is a composition in the form of an aqueous solution that includes: (i) an effective amount of one or more agents for causing eukaryotic cell membrane lysis; (ii) optionally an effective amount of an RNase; (iii) an effective amount of a NAD; (iv) optionally a suitable concentration of counting beads; and (v) an effective amount of one or more, two or more, or three or more NAESA/L against nuclei-associated epitopes. In certain embodiments, the aqueous solution includes components (i)-(v) as identified above. In certain other embodiments, where the NAD is a DNA-specific dye, then the effective amount of RNase, component (ii), can be omitted.

In the several aspects of the invention, particularly preferred combinations of reagents have been identified that are capable of highly selective discrimination of cytotoxicity, genotoxicity with clastogenic mode of action, and genotoxicity with aneugenic mode of action. Preferably, each of these combinations includes, without limitation, a NAD, a first NAESA/L that binds specifically a nuclei-associated epitope associated with double-strand DNA breaks; a second NAESA/L that is responsive to aneugenic activity; and either a third NAESA/L that binds specifically to a third epitope associated with cytotoxicity or a reagent that is responsive to cytotoxicity (e.g., a reagent that labels a marker of mitochondrial health, for instance a mitochondrial membrane-potential dye or luminescent ATP-specific reagent, or is a reagent that is otherwise responsive to cytotoxicity). Particularly preferred combinations of reagents include, without limitation, (i) a NAD, a first NAESA/L that binds specifically to an epitope present on phosphorylated γH2AX, a second NAESA/L that binds specifically to an epitope present on phosphorylated H3, and a third NAESA/L that binds specifically to an epitope present on cleaved caspase 3 or cleaved PARP; (ii) a NAD, a first NAESA/L that binds specifically to an epitope present on phosphorylated γH2AX, a second NAESA/L that binds specifically to an epitope present on phosphorylated H3, and a DNA dye that penetrates dead and dying cells, but not viable cells, such as the photoactivatable dyes EMA or PMA; (iii) a NAD, a first NAESA/L that binds specifically to an epitope present on phosphorylated γH2AX, a second NAESA/L that binds specifically to an epitope present on phosphorylated H3, and a mitochondrial membrane dye such as TMRE; (iv) a NAD, a first NAESA/L that binds specifically to an epitope present on phosphorylated γH2AX, a second NAESA/L that binds specifically to an epitope present on phosphorylated H3, and a reagent that measures cellular ATP levels; (v) a NAD, a first NAESA/L that binds specifically to an epitope present on cleaved PARP, and a second NAESA/L that binds specifically to an epitope present on cleaved caspase 3 and/or 7 and/or 9; and (vi) a NAD, a first NAESA/L that binds specifically to an epitope present on phosphorylated-H3, and either a second NAESA/L that binds specifically to an epitope present on Ki-67 or proliferating cell nuclear antigen (PCNA) or the dye carboxyfluorescein N-succinimidyl ester (CFSE), which are markers of cell proliferation. In addition to the foregoing combinations, counting beads can be incorporated into the combinations to provide information on absolute nuclei (and, thus, cell) counts.

The methods described herein provide for the assessment of eukaryotic cell nuclei for biomarkers of DNA damage and/or transcription factor activation, activity, or expression levels and/or epigenetic modifications to chromatin or chromatin-associated structures using, preferably, flow cytometry, image analysis, imaging flow cytometry, or laser-scanning cytometry. The invention also teaches useful strategies for combining nuclear and other biomarkers into a matrix that is capable of determining genotoxicants' primary mode of DNA-damaging activity. The primary advantage of this methodology relative to other procedures is that these assessments are made very efficiently, through the use of a so-called homogenous (combine and read) assay. The need for such a homogenous assay is met by providing a detergent-based solution that combines cytoplasmic membrane lysis, retention of nuclear envelopes, degradation of RNA, pan-chromatin fluorescent staining, and optionally the fluorescent labeling of nuclei-associated epitope(s) of interest in one simple step. This minimizes time and effort spent handling a sample for evaluation, and therefore affords significant savings in acquiring the much-needed information for evaluating nuclei biomarkers for DNA damage, transcription factor activity, activation, or expression levels, or epigenetic modifications to chromatin or chromatin-associate factors. Furthermore, the accompanying Examples demonstrate methods for building a matrix of nuclei biomarkers that effectively elucidate genotoxic mode of action by facilitating characterization of in vitro cytogenetic damage resulting from clastogenic activity, aneugenic activity, or a consequence of cytotoxicity. Importantly, the methods and kits described herein provide for simultaneous analysis of multiple endpoints, that is, in a "multiplexed" manner, a characteristic that greatly enhances assay efficiency and information content. This, too, is demonstrated in the accompanying Examples where the multiplexed analysis of several endpoints affords comprehensive and efficient acquisition of several nuclei-associated endpoints in a single assay format.

DETAILED DESCRIPTION OF THE INVENTION

Figure 1:
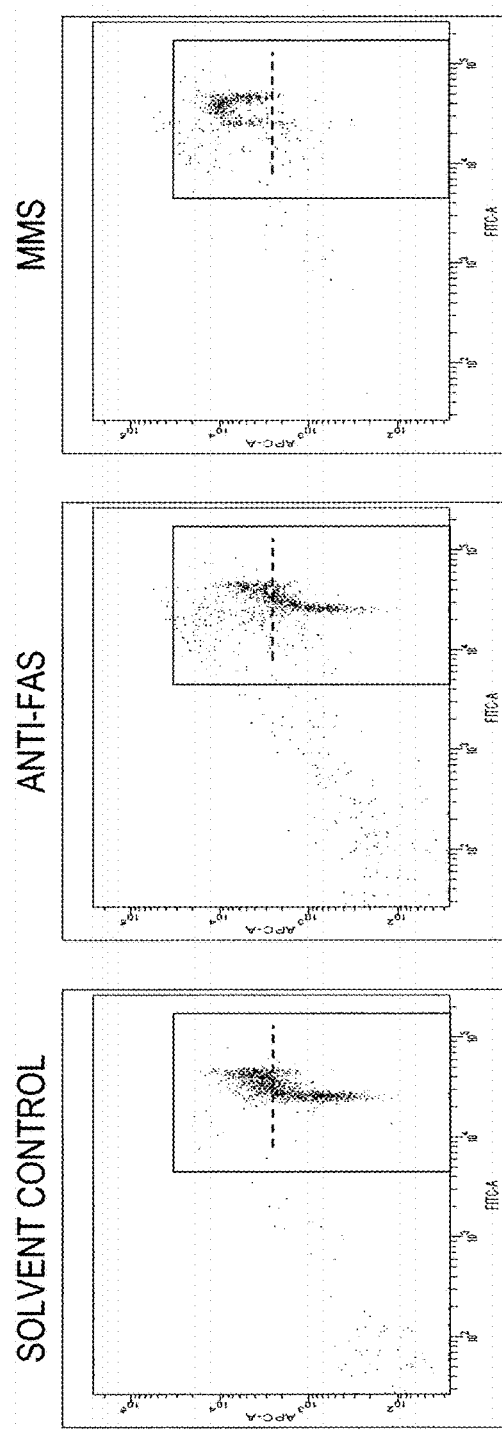
FIG. 1 shows flow cytometric bivariate plots of TK6 cells treated with solvent (DMSO), the apoptosis-inducing agent anti-FAS, or the clastogen methyl methanesulfonate (MMS). The X-axis corresponds to fluorescence associated with the nucleic acid dye SYTOX® Green, and the Y-axis shows fluorescence associated with anti-γH2AX. Following MMS treatment, nuclei's median anti-γH2AX-associated fluorescence intensity is visibly increased. This can be expressed as change in mean or median anti-γH2AX-associated fluorescence intensity relative to solvent control. The apoptosis-inducing agent anti-FAS does not have this effect on TK6 cells. Note that in the case of the γH2AX biomarker, it is preferable to only consider fluorescence for those events that fall within rectangular regions, as shown here. Higher anti-γH2AX-associated fluorescence intensity, i.e., beyond the rectangles, tends to be due to apoptotic cells as opposed to cells with clastogen-induced double-strand DNA breaks. Also note that the dashed lines have been added for illustrative (reference) purposes only.

The present invention is directed to a method for evaluating free eukaryotic cell nuclei for biomarkers of DNA damage and/or transcription factor activation, activity, or expression levels and/or epigenetic modifications to chromatin or chromatin-associated factors. The invention also teaches useful strategies for combining nuclear and other biomarkers into a matrix that is capable of determining genotoxicants' primary mode of DNA-damaging activity.

One aspect of the present invention relates to a method for analyzing detergent-liberated nuclei and/or chromatin debris for nuclei-associated epitopes. The method involves contacting a sample containing eukaryotic cells with a detergent-containing solution that digests outer cytoplasmic membranes, but not nuclear membranes, and that aggregates metaphase chromosomes into bundles of chromosomes. The detergent-containing solution contains RNase to effectively degrade RNA, a fluorescent nucleic acid dye (NAD) to label all chromatin, and one or more nuclei-associated epitope-specific antibodies or other high affinity ligands (NAESA/L) that specifically recognize nuclei-associated epitope(s) of interest. The NAD and NAESA/L fluorescent reagents are excited with light of appropriate excitation wavelength(s). The fluorescent emission and light scatter produced by the nuclei and/or chromatin debris are detected. Any one or more of the following events can be counted: the number of nuclei, the number of NAESA/L-positive nuclei, the number of chromatin debris, the number of NAESA/L-positive chromatin debris, the number of nuclei in G1, S, and G2/M phases of the cell cycle, the number of polyploid nuclei, and NAESA/L-positive nuclei fluorescence intensity.

A number of different endpoints can be determined from these counts, including: the frequency of NAESA/L-positive nuclei relative to total nuclei, and the frequency of NAESA/L-positive chromatin debris relative to total chromatin debris and/or total nuclei, the proportion of nuclei in G1, S, and G2/M phases of the cell cycle, the proportion of polyploid nuclei, and mean and/or median NAESA/L-associated fluorescence intensity.

As indicated above, the frequency of NAESA/L-positive nuclei, chromatin debris, polyploid nuclei, etc., can be expressed relative to other populations, for instance NAESA/L-positive nuclei can be expressed relative to total nuclei. Alternatively, these populations can be expressed per unit volume of sample or per unit time (based on the fluidic rate and the time taken to analyze the sample). Alternatively, counting beads can be added to the sample and the fluorescent emission and light scatter of the counting beads is detected and enumerated along with the other events to obtain an event-to-bead ratio. When utilized, the counting beads can be included in the one or more lysis solution(s) or separately introduced to the sample before or after introduction of the one or more lysis solution(s). The counting beads can be a suspension of relatively uniform particle (e.g., formed of latex or a polymer) that can be readily differentiated from the cells. Preferred counting beads include, without limitation, COUNTBRIGHT™ Absolute Counting Beads and 6 micron PEAK FLOW™ fluorescent microspheres from Life Technologies, and SPHERO™ multi-fluorophore beads from Spherotech Inc. In one embodiment of the present invention, such counting beads are added along with the NAD and NAESA/L-containing lysis solution. However, it will be appreciated by those knowledgeable in the art that there are alternate and equally acceptable times during the procedure when counting beads can be added and used effectively to obtain the desired values.

In certain embodiments, an additional reagent can be introduced that is responsive to cytotoxicity. In one embodiment, this additional reagent is in the form of a DNA dye that penetrates dead and dying cells, but not viable cells, such as the photoactivatable dyes ethidium monoazide bromide or propidium monoazide bromide (see U.S. Pat. Nos. 7,445,910 and 7,645,593 to Dertinger et al., which are hereby incorporated by reference in its entirety), a mitochondrial membrane potential dye, or a reagent that measures cellular ATP levels, e.g., a luminescent reagent such as luciferase/luciferin (Promega's CELLTITER-GLO® kit). Exemplary mitochondrial membrane potential dyes include, without limitation, tetramethylrhodamine ethyl ester (TMRE); tetramethylrhodamine methyl ester (TMRM); 3,3' dihexyloxacarbocyanine iodide ($DiOC_6$); 5,5',6,6'-tetrachloro-1,1',3,3'-tetraethylbenzimidazolcarbocyanine iodide (JC-1); 3,3-dimethyl-α-naphthoxacarbocyanine iodide (JC-9); 1,1',3,3,3',3'-hexamethylindodicarbocyanine iodide ($DilC_1$); nonylacridine orange; safranine O; or rhodamine-123.

Exemplary endpoints for assessing cytotoxicity include, without limitation, NAD-positive nuclei to time ratios, which are responsive to treatment-related changes to cell densities when compared to negative control cells; increased NAESA/L-fluorescence specific for cleaved PARP or any one of cleaved caspases 3, 7, and 9, which indicate activation of cell apoptotic pathways; ethidium monoazide bromide (EMA)- or propidium monoazide bromide (PMA)-positive events as an indicator of (low) membrane integrity; tetramethylrhodamine ethyl ester (TMRE) negative cells as an assessment of mitochondrial membrane potential, and total ATP as measured using luciferase/luciferin as an indicator of overall cell energy stores and reflect overall cell health.

Eukaryotic cells suitable for carrying out the methods of the present invention include any types of animal cells, preferably mammalian cells, as well as plant protoplasts. Exemplary animal cells suitable for carrying out the methods of the present invention include, without limitation, immortalized cell lines, as well as cells which have only recently been harvested from animal species (e.g., primary cell cultures). The eukaryotic cells can be cultured in vitro.

Preferred primary cell cultures are those that divide in culture (i.e., with appropriate growth media, which for some cell types requires the inclusion of cytokines and/or other factors such as mitogens). Exemplary cell types that can be screened easily using the methods of the present invention include, without limitation, blood-, spleen-, lymph node-, or thymus-derived lymphocytes, bone marrow-derived cells including stem cells, and hepatocytes.

Exemplary immortalized cell lines include, without limitation, TK6, AHH-1, WIL-2NS, HepG2, HepaRG™, HeLa, MCF-7, MCL-5, NIH-3T3, Jurkat, HL-60, A549, Raji, CHO-K1, V79, Vero, Hepal cic7, and L5178Y cells, as well as induced pluripotent stems cells.

The NAD reagent can be any dye that permeates the nuclear envelope and imparts fluorescence to chromatin. Any suitable NAD with appropriate excitation and emission spectra can be employed, such as propidium iodine, ethidium bromide, 7AAD, DRAQ 5, DRAQ 7, DAPI, Hoechst 33258, Hoechst 33342, YO-PRO®-1, SYTOX® Green, SYBR® Green I, SYTOX® Red, SYTO® 11, SYTO® 12, SYTO® 13, SYTO® 59, BOBO®, YOYO®, and TOTO®. The need for contact with RNase is eliminated when DNA-specific nucleic acid dyes are used, for instance as is the case for DAPI, Hoechst 33258, and Hoechst 33342. Effective amounts of these dyes will vary depending on the fluorescent properties of the dye, but generally these dyes can be introduced in an amount of about 0.1 µg/ml to about 15 µg/ml.

The one or more lysis solutions can be any suitable lysis solution, or combination thereof, for cell membrane lysis. Non-ionic detergents are particularly desirable for use in the one or more lysis solutions. According to one embodiment, the lysis solution consists of NaCl, Na-Citrate, and octylphenyl-polyethylene glycol (IGEPAL®, Sigma) in deionized water. Alternative embodiments include, without limitation, 0.1% to 10% of one or more of IGEPAL®, TritonX, Tween20, Tween80, and saponin in buffered solution, e.g., PBS.

Suitable NAESA/L reagents specifically bind to nuclei-associated epitopes and have a fluorescent emission spectrum that does not significantly overlap with the emission spectrum of the NAD. Preferred NAESA/L reagents are those that are responsive to DNA damage and/or transcription factor activation, activity, or expression levels and/or epigenetic modifications to chromatin.

In accordance with these aspects of the present invention, exemplary categories of NAESA/L target structures include, without limitation, histone and histone-like proteins as well as histone modifications, whether defined as post-translational or otherwise, markers of cells in metaphase, markers of apoptosis, markers of DNA damage checkpoints/response, transcription factors, DNA adducts, DNA methylation sites, proteins associated with DNA methylation, proteins associated with histone modification, and markers of cell proliferation.

Exemplary histone and histone-like proteins include, without limitation, histone 1 (H1), histone 2A (H2A), histone 2A.Z (H2A.Z), histone 2AX (H2AX), histone 3 (H3), histone 4 (H4), centromere protein A (CENP-A), centromere protein B (CENP-B), centromere identifier (CID), heterochromatin protein (HP1). Exemplary histone modifications include, without limitation, acetylation, methylation, phosphorylation, ubiquitination, glycosylation, ADP-ribosylation, carbonylation, and SUMOylation. A number of commercially available NAESA/L are available against these targets. Specific targets in this category and their NAESA/L include, without limitation, phosphorylated γH2AX and anti-pSer139-γH2AX; phosphorylated-H3 and anti-pSer10-H3, anti-pSer28-H3, or anti-pThr11-H3; HpTGEKP motif and its antibodies; acetylated-H3 and anti-K27ac-H3; methylated-H3 and anti-K4me3-H3; ubiquinated H2B and anti-K12ub1-H2B.

An exemplary marker of cells in metaphase includes, without limitation, Mitotic Protein. A number of commercially available NAESA/L are available against these targets. One specific target and its NAESA/L includes, without limitation phosphorylated Mitotic Protein and the phospho-Ser/Thr-Pro Mitotic protein monoclonal #2 (MPM2).

Exemplary markers of apoptosis include, without limitation, cleaved PARP, and cleaved caspase 3, 7, or 9. A number of commercially available NAESA/L are available against these targets.

Exemplary markers of DNA damage checkpoints/response include, without limitation, ChK1 and ChK2, ATM, ATR, BRCA1, BRCA2, RAD51, and p53. A number of commercially available NAESA/L are available against these targets.

Exemplary transcription factor targets include, without limitation, cAMP response element-binding protein (CREB), CREB-binding protein (CBP), NFKB, aryl hydrocarbon receptor (AhR), and aryl hydrocarbon receptor nuclear translocator (ARNT). A number of commercially available NAESA/L are available against these targets.

Exemplary DNA adducts include, without limitation, O-6-methylguanine, 7-methylguanine, 8-oxo-deoxyguanosine, 1,N(2)-propane deoxyguanosines, and 8-oxo-7,8-dihydro-2'-deoxyguanosine. A number of commercially available NAESA/L are available against these targets.

Exemplary DNA methylation sites include, without limitation, 5-methyl cytidine, 5-carboxylcytosine, 5-formylcytosine, 5-hydroxymethylcytosine, and 3-methylcytosine. A number of commercially available NAESA/L are available against these targets.

Exemplary proteins associated with DNA methylation include, without limitation, DNA methyltransferase 1 (DNMT1), DNA methyltransferase 2 (DNMT2), DNA methyltransferase 3A (DNMT3A), DNA methyltransferase 3B (DNMT3B), and DNA methyltransferase 3-like protein (DNMT3L), and methyl CPG-binding proteins. A number of commercially available NAESA/L are available against these targets.

Exemplary proteins associated with histone modification include, without limitation, histone acetyltransferase (HAT), histone deacetylase (HDAC), histone demethylase (HDME), and sirtuin 2. A number of commercially available NAESA/L are available against these targets. One specific target and its NAESA/L includes, without limitation, phosphorylated SIRT2 and the anti-phospho-Ser331-SIRT2.

Exemplary markers of cell proliferation include, without limitation, proliferating cell nuclear antigen (PCNA) and Ki-67. A number of commercially available NAESA/L are available against these targets. Alternatively, the dye carboxyfluorescein succinimidyl ester (CFSE) can be used as a marker of cell proliferation, because its fluorescence is cut roughly in half as cells divide.

NAESA/L in the form of antibodies that bind specifically to one or more of the exemplary biomarkers that contain the nuclei-associated epitopes are commercially available. Also encompassed by the definition of NAESA/L are binding portions of such antibodies, including monovalent Fab fragments, Fv fragments (e.g., single-chain antibody, scFv), and single variable $V_H$ and $V_L$ domains, and the bivalent $F(ab')_2$ fragments, Bis-scFv, diabodies, triabodies, minibodies, etc. These antibody fragments can be made by conventional procedures, such as proteolytic fragmentation procedures, as described in James Goding, MONOCLONAL ANTIBODIES:PRINCIPLES AND PRACTICE 98-118 (Academic Press, 1983) and Ed Harlow and David Lane, ANTIBODIES: A LABORATORY MANUAL (Cold Spring Harbor Laboratory, 1988); Houston et al., "Protein Engineering of Antibody Binding Sites: Recovery of Specific Activity in an Anti-Digoxin Single-Chain Fv Analogue Produced in *Escherichia coli*," *Proc. Natl. Acad. Sci. USA* 85:5879-5883 (1988); Bird et al, "Single-Chain Antigen-Binding Proteins," *Science* 242:423-426 (1988), which are hereby incorporated by reference in their entirety, or other methods known in the art.

Antibody mimics can also serve as NAESA/L in the present invention. A number of antibody mimics are known in the art including, without limitation, those known as monobodies, which are derived from the tenth human fibronectin type III domain ($^{10}$Fn3) (Koide et al., "The Fibronectin Type III Domain as a Scaffold for Novel Binding Proteins," *J. Mol. Biol.* 284:1141-1151 (1998); Koide et al., "Probing Protein Conformational Changes in Living Cells by Using Designer Binding Proteins: Application to the Estrogen Receptor," *Proc. Natl. Acad. Sci. USA* 99:1253-1258 (2002), each of which is hereby incorporated by reference in its entirety); and those known as affibodies, which are derived from the stable alpha-helical bacterial receptor domain Z of staphylococcal protein A (Nord et al., "Binding Proteins Selected from Combinatorial Libraries of an alpha-helical Bacterial Receptor Domain," *Nature Biotechnol.* 15(8):772-777 (1997), which is hereby incorporated by reference in its entirety). These monobodies and affibodies can be screened and selected for their binding affinity to one or more of the above-identified biomarkers that contain the nuclei-associated epitopes.

Another form of antibody mimic is a nucleic acid aptamer, which can be formed of DNA or RNA or modified nucleotides, and is characterized by specificity for one or more of the above-identified biomarkers that contain the nuclei-associated epitopes. Aptamers are single-stranded, partially single-stranded, partially double-stranded, or double-stranded nucleotide sequences, advantageously a replicatable nucleotide sequence, capable of specifically recognizing a selected non-oligonucleotide molecule or group of molecules by a mechanism other than Watson-Crick base pairing or triplex formation. Aptamers include, without limitation, defined sequence segments and sequences comprising nucleotides, ribonucleotides, deoxyribonucleotides, nucleotide analogs, modified nucleotides and nucleotides comprising backbone modifications, branchpoints and non-nucleotide residues, groups or bridges. Identifying suitable nucleic acid aptamers basically involves selecting aptamers that bind specifically to one or more of the above-identified biomarkers that contain the nuclei-associated epitopes with sufficiently high affinity (e.g., Kd=20-50 nM) and specificity from a pool of nucleic acids containing a random region of varying or predetermined length (Shi et al., "A Specific RNA Hairpin Loop Structure Binds the RNA Recognition Motifs of the Drosophila SR Protein B52," Mol. Cell Biol. 17:1649-1657 (1997); Shi, "Perturbing Protein Function with RNA Aptamers" (thesis, Cornell University) microformed on (University Microfilms, Inc. 1997), each of which is hereby incorporated by reference in their entirety). This procedure is known as SELEX. The SELEX scheme is described in detail in U.S. Pat. No. 5,270,163 to Gold et al.; Ellington and Szostak, "In Vitro Selection of RNA Molecules that Bind Specific Ligands," *Nature* 346:818-822 (1990); and Tuerk & Gold, "Systematic Evolution of Ligands by Exponential Enrichment: RNA Ligands to Bacteriophage T4 DNA Polymerase," *Science* 249:505-510 (1990), each of which is hereby incorporated by reference in its entirety.

Nucleic acid aptamers include multivalent aptamers and bivalent aptamers. Methods of making bivalent and multivalent aptamers are described in U.S. Pat. No. 6,458,559 to Shi et al., which is hereby incorporated by reference in its entirety. A method for modular design and construction of multivalent nucleic acid aptamers, their expression, and methods of use are described in U.S. Patent Publication No. 2005/0282190 to Shi et al, which is hereby incorporated by reference in its entirety.

NAESA/L are preferably labeled with a dye or fluorophore that exhibits a distinct spectral emission relative to the NAD, allowing the NAES/L label to be discriminated from the NAD emissions. Exemplary dyes or fluorophores include, without limitation, ALEXA® dyes from Life Technologies, DYLIGHT™ dyes from Norus Biologics, CF™ dyes available from Biotium Inc., and fluorochromes like FITC and PE. The NAESA/L can be introduced in any amount that is effective to label the epitope of interest, typically about 0.5 µg/ml to about 5.0 µg/ml.

In one embodiment of the methods of the present invention, contacting the sample with one or more lysis solutions and contacting the free nuclei and/or chromatin debris with RNase (optional), a NAD, and one or more NAESA/Ls is carried out simultaneously. Alternatively, these steps are carried out sequentially.

Suitable NAD and NAESA/L reagents are capable of labeling cellular DNA and/or nuclei-associated epitopes of interest at a concentration range detectable by flow cytometry, image analysis, and/or laser-scanning cytometry, and have fluorescent emission spectrums that do not substantially overlap. It should be appreciated by those of ordinary skill in the art that additional fluorescent NAD and NAESA/L reagents are known and are continually being identified. Any suitable reagent with requisite binding specificity and fluorescence characteristics can be employed.

Single-laser flow cytometric analysis uses a single focused laser beam with an appropriate emission band to excite the NAD and NAESA/L fluorochromes. As labeled nuclei, chromatin debris, and optional counting beads pass through the focused laser beam, they exhibit a fluorescent emission maxima characteristic of the fluorescent reagent(s) associated therewith. Dual- or multiple-laser flow cytometric analysis uses two or more focused laser beams with appropriate emission bands in much the same manner as described for the single-laser flow cytometer. Different emission bands afforded by the two or more lasers allow for additional combinations of fluorescent reagents to be employed, and represents a preferred analytical platform for conducting the assay when several fluorochromes are utilized.

Preferably, the flow cytometer is equipped with appropriate detection devices to enable detection of the fluorescent emissions and light scatter produced by the nuclei and chromatin debris and, if used, counting beads. These "light scatter" signals serve as additional criteria that help discriminate nuclei, chromatin debris, and counting beads from one another.

A further aspect of the present invention relates to a method of assessing a singular nuclear biomarker for its responsiveness to external stimuli, for instance a chemical or physical agent. This method involves exposing eukaryotic cells to a chemical or physical agent. In a preferred embodiment of the methods of the present invention, the cells are then contacted with a lysis solution that includes RNase, a NAD, and one NAESA/L reagent. Samples are then analyzed for the number of nuclei, the number of NAESA/L-positive nuclei, mean and/or median NAESA/L-associated fluorescence intensity, and optionally the number of chromatin debris, the number of NAESA/L-positive chromatin debris, the number of nuclei in G1, S, and G2/M phases of the cell cycle, the number of polyploid nuclei, and the number of counting beads. A significant deviation in these values, especially the frequency of NAESA/L-positive events and/or mean NAESA/L-associated fluorescence intensity relative to a baseline value in unexposed or negative control eukaryotic cells, indicates the chemical or physical agent's ability to affect the amount and/or activity of the nuclear biomarker being studied.

Physical agents that are known to affect DNA and/or other nuclei-associated epitopes include, without limitation, heat, cold, gamma, alpha, and beta radiation, and UV radiation.

Chemical agents which are known to affect DNA and/or other nuclei-associated epitopes include, without limitation, tumor promoters including phorbol esters and dioxin-like chemicals, inorganic genotoxicants (e.g., arsenic, cadmium and nickel), organic genotoxicants (for instance those used as antineoplastic drugs, such as cyclophosphamide, cisplatin, vinblastine, cytosine arabinoside, and others), antimetabolites (for instance those used as antineoplastic drugs, such as methotrexate and 5-fluorouracil), organic genotoxicants that are generated by combustion processes (for instance polycyclic aromatic hydrocarbons such as benzo(a)pyrene), certain protein kinase inhibitors, as well as organic genotoxicants that are found in nature (e.g., aflatoxins such as aflatoxin B1).

A further aspect of the present invention relates to a method of assessing multiple nuclear biomarkers for their responsiveness to external stimuli, for instance a chemical or physical agent. This method involves exposing eukaryotic cells to a chemical or physical agent. In a preferred embodiment of the methods of the present invention, the cells are then contacted with a lysis solution that includes RNase, a NAD, and one or more NAESA/L reagents. Based on the number of nuclear biomarkers being investigated and the capabilities of the analytical detection equipment, it may be necessary to consider each of the multiple NAESA/Ls one at a time (i.e., over several parallel samples) in order to optimally detect each NAESA/L. Alternatively, the multiple NAESA/Ls can be detected simultaneously following their use in a single sample. Samples are analyzed for the number of nuclei, the number of NAESA/L-positive nuclei, mean and/or median NAESA/L-associated fluorescence intensity, and optionally the number of chromatin debris, the number of NAESA/L-positive chromatin debris, the number of nuclei in G1, S, and G2/M phases of the cell cycle, the number of polyploid nuclei, and the number of counting beads. A significant deviation in these values, especially the frequencies of NAESA/L-positive events and/or mean NAESA/L-associated fluorescence intensity relative to baseline values in unexposed or negative control eukaryotic cells, indicates the chemical or physical agent's ability to affect the amount and/or activity of the nuclear biomarkers being studied.

A further aspect of the present invention relates to a method of assessing multiple nuclear biomarkers for their responsiveness to external stimuli, for instance a chemical or physical agent, and using the resulting information to classify the agents according to predefined categories. This method involves exposing eukaryotic cells to a chemical or physical agent. In a preferred embodiment of the methods of the present invention, the sample is contacted with a lysis solution that includes RNase, a NAD, and one or more NAESA/L reagents. Based on the number of nuclear biomarkers and the capabilities of the analytical detection equipment, it may be necessary to consider each of the multiple NAESA/Ls one at a time (i.e., over several parallel samples) in order to optimally detect each NAESA/L. Alternatively, the multiple NAESA/Ls can be detected simultaneously following their use in a single sample. Samples are analyzed for the number of nuclei, the number of NAESA/L-positive nuclei, mean and/or median NAESA/L-associated fluorescence intensity, and optionally the number of chromatin debris, the number of NAESA/L-positive chromatin debris, the number of nuclei in G1, S, and G2/M phases of the cell cycle, the number of polyploid nuclei, and the number of counting beads. A significant deviation in these values, especially the frequencies of NAESA/L-positive events and/or mean NAESA/L-associated fluorescence intensity relative to baseline values in unexposed or negative control eukaryotic cells, indicates the chemical or physical agent's ability to affect the amount and/or activity of the nuclear biomarkers being studied. By considering the biomarkers' responsiveness and/or response magnitude, a statistical method is used to predict a category that best describes the chemical or physical agent. In a preferred embodiment of the present invention, logistic regression and/or discriminant analysis is used to predict a category and provide a measure of confidence associated with the prediction.

A further aspect of the present invention relates to a method of assessing multiple nuclear biomarkers for their responsiveness to external stimuli, for instance a chemical or physical agent, and using the resulting information to classify the agents according to genotoxic mode of action. This method involves exposing eukaryotic cells to a chemical or physical agent. In a preferred embodiment of the methods of the present invention, the sample is contacted with a lysis solution that includes RNase, a NAD, and one or more NAESA/L reagents. Based on the number of nuclear biomarkers and the capabilities of the analytical detection equipment, it may be necessary to consider each of the multiple NAESA/Ls one at a time (i.e., over several parallel samples) in order to optimally detect each NAESA/L. Alternatively, the multiple NAESA/Ls can be detected simultaneously following their use in a single sample. Samples are analyzed for the number of nuclei, the number of NAESA/L-positive nuclei, mean and/or median NAESA/L-associated fluorescence intensity, and optionally the number of chromatin debris, the number of NAESA/L-positive chromatin debris, the number of nuclei in G1, S, and G2/M phases of the cell cycle, the number of polyploid nuclei, and the number of counting beads. A significant deviation in these values in unexposed or negative control eukaryotic cells is indicative of the chemical or physical agent's genotoxic mode of action. By considering the biomarkers' responsiveness and/or response magnitude, a statistical method is used to predict a category to describe the chemical or physical agent. In a preferred embodiment of the present invention, logistic regression and/or discriminant analysis is used to predict a category, for example cytotoxic, genotoxic with a clastogenic MOA, or genotoxic with an aneugenic MOA, and provide a measure of confidence associated with the prediction.

In the several aspects of the invention, particularly preferred combinations of reagents have been identified that are capable of highly selective discrimination of cytotoxicity, genotoxicity with clastogenic mode of action, and genotoxicity with aneugenic mode of action. Preferably, each of these combinations includes, without limitation, a NAD, a first NAESA/L that binds specifically a nuclei-associated epitope associated with double-strand DNA breaks; a second NAESA/L that is responsive to aneugenic activity; and a third reagent that is either a NAESA/L that binds specifically to an epitope associated with cytotoxicity or a dye responsive to cytotoxicity. Particularly preferred combinations of reagents include, without limitation, (i) a NAD, a first NAESA/L that binds specifically to an epitope present on phosphorylated γH2AX, a second NAESA/L that binds specifically to an epitope present on phosphorylated H3, and a third NAESA/L that binds specifically to an epitope present on cleaved caspase 3 or cleaved PARP; (ii) a NAD, a first NAESA/L that binds specifically to an epitope present on phosphorylated γH2AX, a second NAESA/L that binds specifically to an epitope present on phosphorylated H3, and a DNA dye that penetrates dead and dying cells, but not viable cells, such as the photoactivatable dyes ethidium monoazide bromide or propidium monoazide bromide; (iii) a NAD, a first NAESA/L that binds specifically to an epitope present on phosphorylated γH2AX, a second NAESA/L that binds specifically to an epitope present on phosphorylated H3, and a mitochondrial membrane potential dye such as TMRE; (iv) a NAD, a first NAESA/L that binds specifically to an epitope present on phosphorylated γH2AX, a second NAESA/L that binds specifically to an epitope present on phosphorylated H3, and a reagent that measures cellular ATP levels (e.g., a luminescent reagent such as luciferase/D-luciferin); (v) a NAD, a first NAESA/L that binds specifically to an epitope present on cleaved PARP, and a second NAESA/L that binds specifically to an epitope present on cleaved caspase 3 and/or 7 and/or 9; and (vi) a NAD, a first NAESA/L that binds specifically to an epitope present on phosphorylated-H3, and either a second NAESA/L that binds specifically to an epitope present on Ki-67 or PCNA, or the dye CFSE, which are markers of cell proliferation. For each of these combinations, in certain embodiments the NAD and NAESA/L are provided in a single lysis solution that also includes RNase and counting beads.

In these several methods for screening the effects of chemical or physical agents on the single or multiple nuclear biomarkers, these methods can be carried out in parallel with, or subsequent to, an analysis according to the methods described in U.S. Pat. Nos. 7,445,910 and 7,645,593 to Dertinger et al., which are hereby incorporated by reference in its entirety, or the methods described in U.S. Patent Application Publ. No. 20140017673 to Dertinger et al., which is hereby incorporated by reference in its entirety. For instance, the methods for scoring an in vitro micronucleus assay as described in these patent references can be used to characterize treatment-related cytotoxicity or genotoxicity, and in the case of the above-identified patent application characterize whether the genotoxic activity is the result of an aneugenic or clastogenic mode of action.

In carrying out the methods of the present invention, exposure of eukaryotic cells to physical or chemical agents is preferably carried out for a predetermined period of exposure time. Preferred exposure times will depend on the target being studied. For example, when considering chemicals for their genotoxic potential, exposure times typically range from about 3 hrs to the equivalent of approximately two population doublings.

Methods of assessing the responsiveness of nuclear biomarkers to physical or chemical agents may further involve a delay between the end of exposure and prior to performing cell harvest, membrane lysis, labeling, and analysis according to the previously described methods of the present invention. When employed, the delay or "recovery" period is preferably between about 1 minute and the equivalent of approximately two population doublings, although longer or shorter delays can also be utilized.

To some degree, exposure time and recovery periods will be cell line- and nuclear biomarker-dependent. Persons of skill in the art can readily optimize the methods of the present invention for different types of eukaryotic cells and different physical or chemical agents.

Certain agents may offer protection from adverse stimuli, while others magnify deleterious effects. The present invention can be used to evaluate the effects of an agent that can modify (i.e., enhance or suppress) such responses. To assess the suspected protective effects of an agent, it can be added to the culture of cells prior to, concurrently with, or soon after addition of a known stressor. Any protective effect afforded by the agent can be measured relative to damage caused by the stressor agent alone. For example, putative protective agents can be vitamins, bioflavonoids and anti-oxidants, dietary supplements (e.g., herbal supplements), or any other protective agent, naturally occurring or synthesized by man.

To assess the ability of an agent to synergistically or additively enhance adverse effects, the agent can be added to the culture of cells prior to, concurrently with, or shortly after addition of a known stressor. Any additive or synergistic effect caused by the agent can be measured relative to deleterious effects caused by either stressor agent alone.

Yet another aspect of the present invention relates to a kit that includes: one or more eukaryotic cell membrane lysis solutions; RNase, a NAD, and instructions for their use. Kits are also provided that may or may not lack one or more of the preceding components (e.g., RNase is optional), and may include one or more of the following components: NAESA/L that recognize specific nuclei-associated epitope(s), instructions for the use of these reagents, and/or a computer-readable medium that contains instructions for statistical analyses for characterizing in vitro genotoxicity as the result of clastogenicity, aneugenicity, or cytotoxicity based on the behavior of a eukaryotic cell in response to exposure to a chemical or physical agent and following exposure to the kit components. These statistical analyses may include logistic regression and/or discriminant analysis. Ideally, the fluorescent emission spectra of the NAD and NAESA/L do not substantially overlap.

In certain embodiments, the one or more eukaryotic cell membrane lysis solution(s) also contain(s) all other reagents supplied with the kit, in which case the kit contains the one or more solutions, preferably a single solution, and optionally the computer-readable medium, and instructions for their use. Thus, a further aspect of the present invention relates to an analytical formulation in the form of an aqueous solution that includes: (i) an effective amount of one or more agents for causing eukaryotic cell membrane lysis, preferably about 0.1% to about 10% of a non-ionic surfactant of the type described above; (ii) an effective amount of an RNase, preferably about 0.05 mg/ml to about 5.0 mg/ml; and (iii) an effective amount of a NAD, preferably about 0.1 µg/ml to about 15 µg/ml. In an alternative embodiment, the analytical formulation may also include (iv) counting beads, preferably in an amount affording a final concentration of about 500 beads/ml to about 50,000 beads/ml. In an alternative embodiment, the analytical formulation may also include, with or without the counting beads, (v) an effective amount of one or more, preferably two or more, or even three or more NAESA/L against distinct nuclei-associated epitopes and/or (vi) an effective amount of a fluorescent or luminescent reagent that is responsive to cytotoxicity, as described above. Effective amounts for each of the one or more NAESA/L is preferably about 0.5 µg/ml to about 5 µl/ml. In yet another embodiment, the analytical formulation includes components (i)-(v) as identified above, or (i)-(vi) as identified above. Finally, for each of the preceding embodiments identified above, where the NAD is a DNA-specific dye, then the effective amount of RNase, component (ii), can be omitted from each of the analytical formulations. In alternative embodiments, the analytical formulation consists of components (i), (iii), (iv); components (i), (iii)-(v); or components (i), (iii)-(vi); any of which may optionally contain component (ii), one or more buffers, one or more stabilizers, and/or one or more preservatives added to the composition.

EXAMPLES

The examples below are intended to exemplify the practice of the present invention but are by no means intended to limit the scope thereof.

Cells and Culture Medium

The TK6 cells used in these experiments were from American Type Tissue Collection (ATCC) (Manassas, Va.). Cells were maintained in culture medium at 37° C., 5% $CO_2$, and in a humid atmosphere. Cells were maintained between approximately $1 \times 10^4$ and $1 \times 10^6$ cells/ml for routine passage. The culture medium consisted of RPMI 1640 supplemented with 2 mM L-glutamine, 100 IU penicillin and 100 µg/ml streptomycin, to which heat inactivated horse serum was added for 10% v/v final concentration (all from MediaTech Inc., Herndon, Va.).

Treatment of Cells with Toxic Agents

For these experiments, TK6 cells were treated with solvent (most often DMSO, 1% v/v) and a range of closely spaced test article concentrations. Treatments occurred in wells of a 96-well plate. At the start of treatment, cells were at $2 \times 10^5$/ml in a volume of 300 µl per well. Counting beads (PEAK FLOW™) were included in these cultures at a concentration of approximately 1 drop per 10 ml, and served as a means to derive relative nuclei to bead ratios (relative to solvent controls). Continuous treatment occurred for approximately 24 hrs, during which time plates were incubated at 37° C., 5% $CO_2$, and in a humid atmosphere. Each test article concentration was studied in 3 to 6 replicate wells.

The γH2AX endpoint described herein was studied 4 and/or 24-27 hrs after start of treatment. Each of the remaining endpoints were studied at the conclusion of the treatment period, that is 24 to 27 hrs after initiation of exposure to test article (which for this cell line corresponds to approximately 1.5 to 2.0 population doubling times).

Liberating and Labeling Nuclei for Flow Cytometric Analysis

At the time of cell harvest (4 hrs and 24 to 27 hrs), cells were resuspended with gentle pipetting and 25 µl aliquots were transferred to wells of a 96 well plate containing 50 µl pre-aliquoted lysis solution. Lysis solution was composed of deionized water, 0.584 mg NaCl/ml, 1 mg sodium citrate/ml, 0.6 µl IGEPAL®/ml, 1 mg RNase A/ml, NAD (0.4 µM SYTOX® Green), counting beads, and as described in more detail below, one of the following NAESA/L reagents: anti-cleaved caspase 3-ALEXA® 647 antibody (5 µl/ml) (Cleaved Caspase-3 (Asp175) (D3E9) Rabbit mAb (Alexa Fluor® 647 Conjugate), Cell Signaling Technology, Danvers, Mass.) or anti-cleaved PARP-ALEXA® 647 (5 µl/ml) (Alexa Fluor® 647 Mouse anti-Cleaved PARP (Asp 214), BD Biosciences, San Jose, Calif.) antibody or anti-γH2AX-ALEXA® 647 antibody (5 µl/ml) (Alexa Fluor® 647 Mouse anti-$H_2AX$ (pS139), BD Biosciences, San Jose, Calif.) or anti-H3-ALEXA® 647 antibody (5 µl/ml) (Alexa Fluor® 647 Rat anti-H3 (pS28), BD Biosciences, San Jose, Calif.).

After incubation at room temperate for at least 5 minutes, samples were analyzed with a dual-laser flow cytometer, 488 nm and 633 nm excitation (FACSCanto II, BD Biosciences, San Jose, Calif.). Instrumentation settings and data acquisition/analysis were controlled with Diva software v6.1.3. SYTOX® Green-associated fluorescence emission was collected in the FITC channel, and ALEXA® 647-associated fluorescence was collected in the APC channel. The BD Biosciences High Throughput Sampler (HTS) attachment was used to automatically analyze each of the samples in the 96 well plate(s). For the majority of these endpoints and experiments, the stop mode was configured such that each well was analyzed for 5 seconds, which usually represented sufficient time to acquire at least 500 NAD-positive nuclei.

Micronucleus Assay

The in vitro micronucleus assay is a chromosomal damage test that is widely used to evaluate chemical and/or physical agents for clastogenic and aneugenic activity. While the sensitivity of the micronucleus test is generally regarded as high, there are ongoing concerns that this and other eukaryotic cell in vitro genotoxicity assays exhibit unacceptably low specificity (i.e., high false positive rates). Furthermore, in the usual conduct of the in vitro micronucleus assay, the discrimination of bona fide genotoxic activity as primarily occurring through a clastogenic or aneugenic mode of action is not readily obtained. Example 4 describes experiments with 20 diverse chemical agents that exhibited positive in vitro micronucleus results. (Clastogens: arabinofuranosyl cytidine, etoposide, methyl methanesulfonate, cisplatin, camptothecin, aphidicoline, 5-fluorouracil, 4-nitroquinoline-1-oxide, and hydroxyurea; aneugens: vinblastine, paclitaxol, carbendazim, griseofulvin, and diethylstilbestrol; cytotoxicants: carbonyl cyanide m-chlorophenyl hydrazone, anti-FAS, nutlin-3, tunicamycin, phenformin HCl, and tributyltin.) The methodology used to score micronuclei in cultures of TK6 cells was commercially available In Vitro MICROFLOW® kits (Litron Laboratories, Rochester, N.Y.). Given continuous exposure to these chemicals (24-27 hrs), 13 of the positive results were expected based on their known clastogenic or aneugenic activity. However, 4 positive findings were regarded false or irrelevant positives, likely attributable to DNA damage that was secondary to cytotoxicity as opposed to DNA-reactivity. These chemicals therefore represented a good opportunity to explore whether one or more nuclear biomarkers, as studied according to present invention, could be used to categorize these in vitro genotoxic-positive compounds as clastogenic, aneugenic, or cytotoxic.

For these experiments, each of the 20 chemicals was tested over closely spaced concentrations, 6 replicate wells per concentration. Three wells were used for the micronucleus analyses, and three wells were used for the several nuclear biomarker assessments of the type described in Example 1. Other endpoints of cytotoxicity were considered, including NAD-positive nuclei to time ratios, ethidium monoazide bromide (EMA) positive events as an indicator of membrane integrity, tetramethylrhodamine ethyl ester (TMRE) negative cells as an assessment of mitochondrial membrane potential, and ATP levels (using luciferase) as an assessment of overall cell health in the sample. We believed that perhaps one but more likely two or more of these nuclei biomarker or other endpoints would provide signatures that would enable us to accurately classify these chemicals into groups according to MOA. Further details are described under Statistical Analyses, as well as Example 4 below.

Statistical Analyses

Logistic regression is considered a part of generalized linear models. Logistic regression allows one to predict a discrete outcome, such as group membership, from a set of explanatory variables that may be continuous, discrete, dichotomous, or any combination of these. Discriminant analysis is a related statistical method that can also be used to predict group membership. In some circumstances there are advantages to logistic regression, because it makes fewer assumptions about the explanatory variables, for instance it does not require normal distribution or equal variances. In Example 4 which follows, the logistic regression platform (JMP software, v 8.0.1, SAS Institute, Inc.) was utilized to construct a model whereby nuclei biomarker and/or other cytotoxicity endpoints were considered for their ability to predict class of chemical agent, that is, either clastogenic, aneugenic, or cytotoxic. This categorization strategy has many potential applications, including following up a positive in vitro chromosomal damage assay result to determine genotoxic MOA.

To build the model, individual explanatory variables, described in more detail in Example 4, were tested for their ability to categorize chemicals into one of three groups. In an iterative process, significant explanatory variables were added to a model with the goal of building the most parsimonious model that correctly categorized each of the 20 chemicals into groups specified a priori.

Example 1

Nuclear Biomarker γH2AX is Responsive to Clastogenic Activity

In this experiment, TK6 cells were treated with the prototypical clastogenic agent methyl methanesulfonate (MMS), or the cytotoxicant anti-FAS. Treatments occurred over a range of closely spaced concentrations. Approximately 24-27 hours after the start of treatment, 25 µl aliquots of cells were added to lysis solution containing RNase, NAC, anti-γH2AX-ALEXA® 647, and counting beads. As shown by Table I, each chemical caused concentration-dependent reductions to nuclei to bead ratios, indicative of fewer cells and therefore cytotoxicity. Whereas the clastogen MMS was observed to cause higher anti-γH2AX-associated fluorescence intensity relative to solvent control wells, no change was evident with the cytotoxicant anti-FAS. See FIG. 1 for representative bivariate plots that illustrate the regions used to make these measurements.

TABLE I

Shift in γH2AX-associated Fluorescence in Response to a Clastogen

| Test Article | Test Article Conc. | Nuclei to Bead Ratio (% of Control) | γH2AX Fluorescence (Fold-Increase)[†] |
|---|---|---|---|
| Solvent Control | 0 | 100 | 1.00 |
| MMS | 2.344 µg/ml | 88 | 3.13 |
| MMS | 3.125 µg/ml | 87 | 4.11 |
| MMS | 4.6875 µg/ml | 83 | 4.36 |
| MMS | 6.25 µg/ml | 78 | 4.92 |
| MMS | 9.375 µg/ml | 64 | 4.79 |
| MMS | 12.5 µg/ml | 58 | 4.80 |
| Anti-FAS | 9.375 ng/ml | 87 | 0.93 |
| Anti-FAS | 12.5 ng/ml | 86 | 0.92 |
| Anti-FAS | 18.75 ng/ml | 80 | 0.94 |
| Anti-FAS | 25 ng/ml | 71 | 0.95 |
| Anti-FAS | 37.5 ng/ml | 66 | 0.98 |
| Anti-FAS | 50 ng/ml | 50 | 1.00 |

[†]Fold Increase is relative to Control

Example 2

Figure 2:
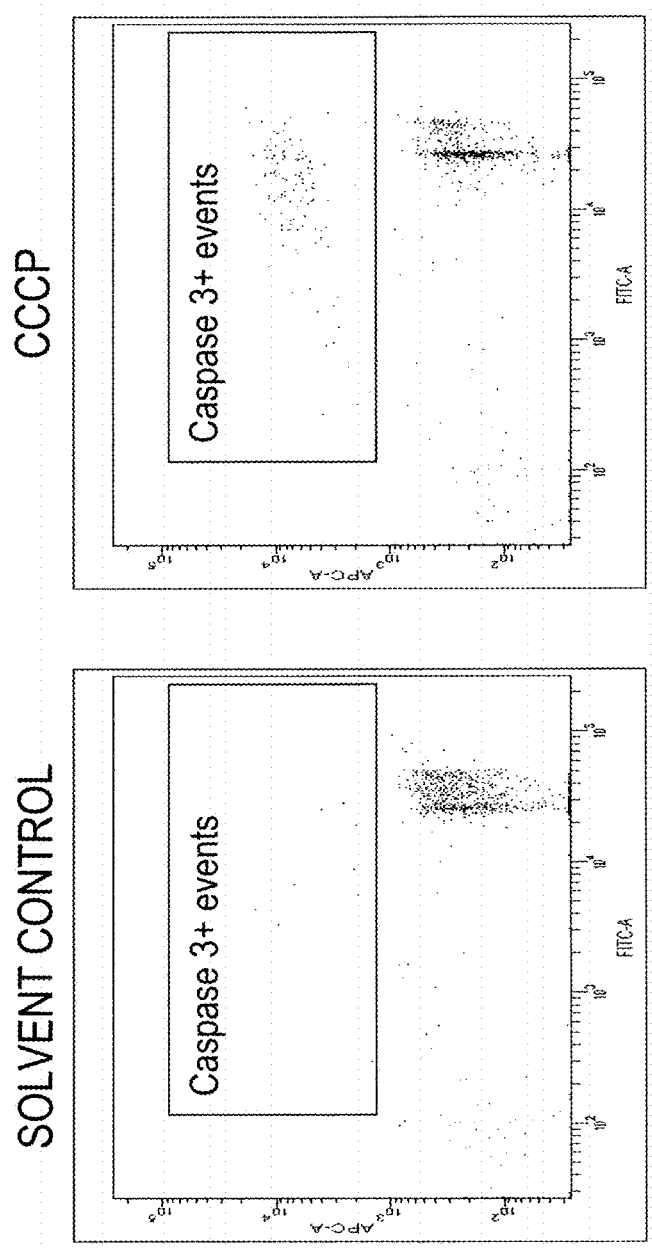
FIG. 2 shows flow cytometric bivariate plots of TK6 cells treated with solvent (DMSO) or the apoptosis-inducing agent carbonyl cyanide m-chlorophenyl hydrazone (CCCP). The X-axis corresponds to fluorescence associated with the nucleic acid dye SYTOX Green, and the Y-axis shows fluorescence associated with anti-cleaved caspase 3. Following CCCP treatment, the percentage of nuclei exhibiting anti-cleaved caspase 3-positive events is visibly increased.

Nuclear Biomarkers PARP and Cleaved Caspase 3 are Responsive to Apoptotic Activity In this experiment, TK6 cells were treated with the prototypical apoptosis-inducing agent carbonyl cyanide m-chlorophenyl hydrazone (CCCP). Treatments occurred over a range of closely spaced concentrations. Approximately 24-27 hours after the start of treatment, 25 µl aliquots of cells were added to lysis solutions containing RNase, NAC, and either anti-cleaved PARP-ALEXA® 647 or anti-cleaved Caspase 3. As shown by Table II, CCCP caused concentration-dependent reductions to nuclei to bead ratios, indicative of fewer cells and therefore cytotoxicity. This chemical was also observed to affect cleaved PARP and Caspase 3 levels in nuclei, as evidenced by the higher values of cleaved PARP- and Caspase 3-positive nuclei relative to solvent control wells. See FIG. 2 for representative bivariate plots that illustrate the regions used to make these measurements.

TABLE II

Cleaved PARP- and Caspase 3-Positive Nuclei in Response to the Cytotoxicant CCCP

| CCCP Conc. (µM) | Nuclei to Bead Ratio (% of Control) | PARP-Positive Nuclei (Fold-Increase)[†] | Caspase 3-Positive Nuclei (Fold-Increase)[†] |
|---|---|---|---|
| 0 | 100 | 1.00 | 1.00 |
| 3.125 | 79 | 4.90 | 2.63 |
| 4.6875 | 69 | 8.60 | 4.33 |
| 6.25 | 64 | 12.1 | 5.86 |
| 9.375 | 59 | 20.75 | 9.13 |
| 12.5 | 50 | 34.45 | 18.83 |

[†]Fold Increase is relative to Control

Example 3

Nuclear Biomarker Phospho-H3 is Responsive to Aneugenic Activity

Figure 3:
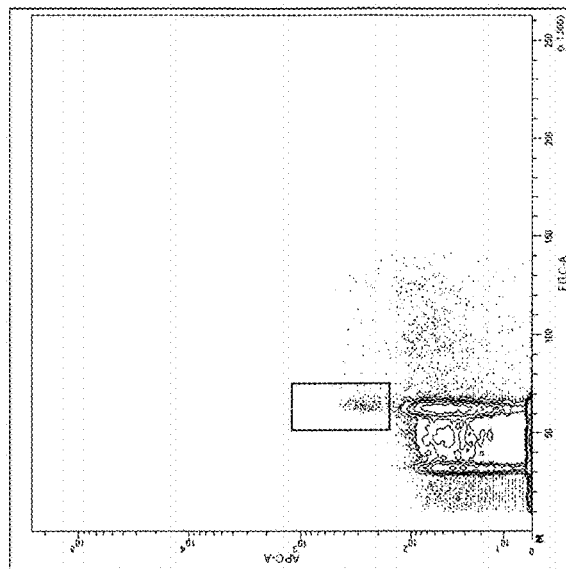
FIG. 3 shows flow cytometric bivariate plots of TK6 cells treated with solvent (DMSO), the aneugen vinblastine, or the clastogen MMS. The X-axis corresponds to fluorescence associated with the nucleic acid dye SYTOX® Green, and the Y-axis shows fluorescence associated with anti-phospho-H3. Following vinblastine treatment, the percentage of nuclei exhibiting anti-phospho-H3-positive events is increased relative to solvent control. The clastogen MMS does not have this effect on TK6 cells.
Figure 3:
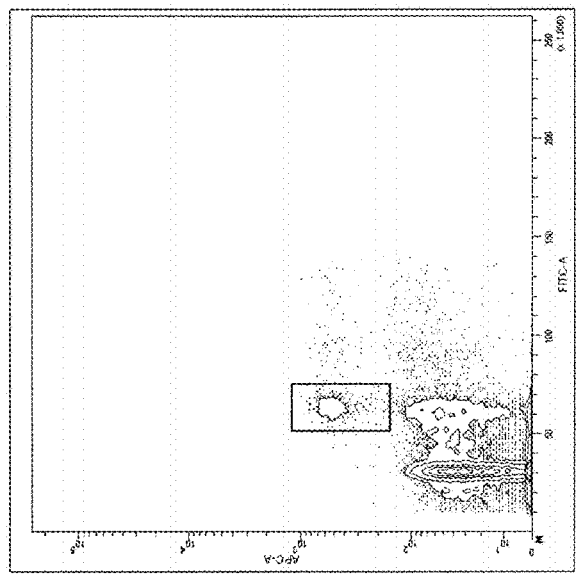
Figure 3:
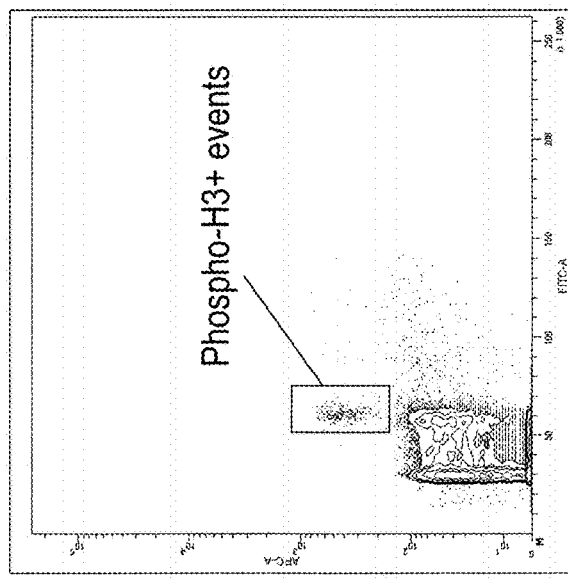

In this experiment, TK6 cells were treated with the prototypical aneugen vinblastine and the prototypical clastogen methyl methanesulfonate (MMS). Treatments occurred over a range of closely spaced concentrations. Approximately 24-27 hours after the start of treatment, 25 µl aliquots of cells were added to lysis solutions containing RNase, NAC, anti-H3-ALEXA® 647 (recognizes phosphoserine 28), and counting beads. As shown by Table III, vinblastine and MMS caused concentration-dependent reductions to nuclei to bead ratios, indicative of fewer cells and therefore cytotoxicity. Whereas the aneugen vinblastine was observed to markedly increase the frequencies of H3-positive nuclei, the clastogen had no such effect. See FIG. 3 for representative bivariate plots that illustrate the regions used to make these measurements.

TABLE III

Phospho-H3-Positive Nuclei in Response to Vinblastine and MMS

| Test Article | Test Article Conc. | Nuclei to Bead Ratio (% of Control) | Phospho-H3+ Nuclei (Fold-Increase)[†] |
|---|---|---|---|
| Solvent Control | 0 | 100 | 1 |
| Vinblastine | 0.3 ng/ml | 98 | .86 |
| Vinblastine | 0.4 ng/ml | 97 | .86 |
| Vinblastine | 0.6 ng/ml | 86 | 1.23 |
| Vinblastine | 0.8 ng/ml | 81 | 2.11 |
| Vinblastine | 1.2 ng/ml | 71 | 4.85 |
| Vinblastine | 1.6 ng/ml | 58 | 5.41 |
| MMS | 2.344 µg/ml | 88 | 1.00 |
| MMS | 3.125 µg/ml | 87 | 0.76 |
| MMS | 4.6875 µg/ml | 83 | 0.67 |
| MMS | 6.25 µg/ml | 78 | 0.71 |
| MMS | 9.375 µg/ml | 64 | 0.76 |
| MMS | 12.5 µg/ml | 58 | 0.65 |

[†]Fold Increase is relative to Control

Example 4

Matrix of Biomarkers Predict Genotoxic Mode of Action

In these experiments, TK6 cells were treated with each of 9 clastogens, 5 aneugens, and 6 cytotoxicants. Each of these agents was observed in previous experiments to induce what appeared to be significant micronucleus responses at concentrations that were deemed moderately but not overly cytotoxic. Those cytotoxicity evaluations were based on a conventional approach for assessing cytotoxicity in genotoxicity tests, that is, relative cell counts (which in the case of the flow cytometry-based In Vitro MICROFLOW® kit is accomplished by measuring nuclei to counting bead ratio or else nuclei to time ratio and expressing these values relative to the mean solvent control value). For the follow-up experiments, treatments occurred over a range of closely spaced concentrations. Approximately 24-27 hours after the start of treatment, three wells per concentration were processed via MICROFLOW® instructions for micronucleus frequencies, relative nuclei to time values, and EMA-positive events (an assessment of membrane integrity). The remaining three wells per concentration were used to accomplish a series of nuclei biomarker readings according to the invention, as well as two other assessments of cytotoxicity—frequency of TMRE-negative cells and ATP levels (via Promega's CELL TITERGLO® kit).

The resulting micronucleus data confirmed the initial experiments by showing significant induction of micronuclei or what appeared to be micronuclei at moderately cytotoxic treatment conditions as evaluated by nuclei to time ratios. (Induction of micronuclei was considered significant when mean fold-increase relative to solvent control was ≥3-fold; moderate but not excessive cytotoxicity was indicated by relative nuclei to time ratios that approached but did fall below 45%.) These results confirm the high sensitivity but low specificity of the in vitro micronucleus assay as currently practiced.

As indicated above, a series of nuclear biomarkers and other endpoints were evaluated for three parallel wells per concentration. In order to reduce the data-rich dose-response data for each experimental endpoint to a single value, two approaches were tested. Each endpoint's mean value corresponding to the lowest effective micronucleus-inducing concentration was recorded. Additionally, each endpoint's mean value corresponding to the highest passing concentration (i.e., highest concentration that approached but did not fall below 45% relative nuclei to time ratio) was recorded. These values, together with our a priori classification for each chemical noted above (i.e., clastogen, aneugen, or cytotoxicant) were analyzed using JMP's logistic regression platform. One initial observation was that more explanatory variables were found to be statistically significant ($p<0.05$) when the data reduction process occurred according to highest passing concentration. Furthermore, when explanatory variables were significant for both lowest micronucleus-inducing effect concentration as well as highest passing concentration, the latter tended to exhibit lower p values and higher $R^2$ values (indicative of a model's goodness of fit). Therefore, the subsequent analyses that are described in more detail below were generated with the data reduction scheme that was based on the highest passing concentration.

Table IV shows p and $R^2$ values, as well as the proportion of correct predictions made by each of the explanatory variables in isolation. Whereas some endpoints were found to be quite effective at classifying one or more of the categories, none was perfectly effective for classifying across all three. The combination of γH2AX fluorescence shift and fold-increase in phospho-H3-positive events was considered a particularly complementary pair of endpoints, as the former is considered an indicator of double-strand DNA breaks and indeed was shown to be effective at classifying clastogens, while the latter is known to be responsive to aneugenicity and showed good potential for detecting agents with this activity. As evidenced by a higher $R^2$ value, the combination of these two nuclear biomarkers was observed to markedly improve the model. However, it was only when these two explanatory variables were combined with a third endpoint that can be generalized as being responsive to cytotoxicity that the most effective model was realized.

TABLE IV

Logistic Regression Output for Classifying In Vitro Micronucleus-Positive Events According to Mode of Action

| Explanatory Variable(s) | p value | $R^2$ | Clastogens Correctly Predicted | Aneugens Correctly Predicted | Cytotoxicants Correctly Predicted | Notes |
|---|---|---|---|---|---|---|
| γH2AX shift (4 hr) | <0.0001 | 0.4621 | 8/9 | 5/5 | 6/6 | Fairly effective across groups |
| γH2AX shift (24-27 hr) | 0.0085 | 0.2236 | 7/9 | 0/5 | 0/6 | Lower predictivity relative to 4 hr time point |
| Phospho-H3+ | <0.0001 | 0.5497 | 7/9 | 5/5 | 3/6 | Tends to misclassify cytotoxicants as clastogens |
| Cleaved Cas3+ | 0.0061 | 0.2387 | 7/9 | 0/5 | 4/6 | Poor ability to classify aneugens |
| Cleaved PARP+ | 0.0014 | 0.3085 | 8/9 | 1/5 | 3/6 | Poor ability to classify aneugens and cytotoxicants |
| TMRE− cells | <0.0001 | 0.4761 | 9/9 | 2/5 | 4/6 | Poor ability to classify aneugens |
| EMA+ events | 0.0006 | 0.3455 | 9/9 | 4/5 | 4/6 | Fairly effective across groups |
| ATP level | <0.0001 | 0.6368 | 8/9 | 3/5 | 5/6 | Fairly effective across groups |
| γH2AX shift (4 hr) Phospho-H3+ | <0.0001 | 0.8325 | 8/9 | 5/5 | 6/6 | One clastogen misclassified as cytotoxicant |
| γH2AX shift (4 hr) Phospho-H3+ Cleaved Cas3+ | <0.0001 | 1.0000 | 9//9 | 5/5 | 6/6 | Zero misclassified |
| γH2AX shift (4 hr) Phospho-H3+ Cleaved PARP+ | <0.0001 | 1.0000 | 9//9 | 5/5 | 6/6 | Zero misclassified |
| γH2AX shift (4 hr) Phospho-H3+ TMRE− Cells | <0.0001 | 1.0000 | 9//9 | 5/5 | 6/6 | Zero misclassified |
| γH2AX shift (4 hr) Phospho-H3+ EMA+ Events | <0.0001 | 1.0000 | 9//9 | 5/5 | 6/6 | Zero misclassified |
| γH2AX shift (4 hr) Phospho-H3+ ATP Level | <0.0001 | 1.0000 | 9//9 | 5/5 | 6/6 | Zero misclassified | p value = the observed significance probability for the Chi-square test;
$R^2$ = the proportion of the total uncertainty that is attributed to the model fit, "goodness of fit"

From the data above, it is reasonable to conclude that a matrix of endpoints that include nuclei biomarkers measured according to methods described by this invention are able to distinguish between clastogens, aneugens, and cytotoxicants. Importantly, logistic regression and related tests are able to make these predictions for new chemicals by adding their data to the statistical program, but in those cases without specifying a priori categories. The resulting models represent powerful tools, as their categorizations are each accompanied by measures of probability, that is, their confidence in a given call.

It appears as though the most effective and parsimonious model for accurately categorizing in vitro micronucleus-positive chemicals into one of three groups can be summarized as follows: i) include at least one sensitive and specific endpoint of double-strand DNA breaks, for instance γH2AX-associated fluorescence shift; and ii) include at least one sensitive and specific endpoint that is responsive to aneugenic activity, for instance frequency of phospho-H3-positive events; and iii) include at least one endpoint that is responsive to cytotoxicity, for instance any one of the following—cleaved caspase 3-positive events, cleaved PARP-positive events, TMRE-negative cells, EMA-positive events, or ATP levels. While these and a multitude of other explanatory variables may be incorporated into such a model, it is known that overly complex models can fail for a variety of reasons, and the goal should therefore be to reduce the model to its simplest yet effective form.

Example 5

Multiplex Assay

This experiment highlights the ability of the invention to combine multiple nuclei-associated endpoints into one flow cytometric analysis. For this experiment, log-phase TK6 cells were treated with cisplatin over a wide range of concentrations and then incubated at 37° C. for 24 hours. Each concentration was studied in triplicate wells of a 96 well plate. After 24 hours, well contents were pipetted up and down several times to form homogenous suspensions, and 25 μl per well was added to wells of a new 96 well plate that contained 50 μl of working lysis/labeling/staining solution. This lysis/labeling/staining solution was comprised of 5 μl anti-γH2AX-Alexa® 488/ml, 1 μl anti-phospho-H3-PE/ml, 5 μl anti-cleaved PARP-Alexa® 647/ml, 5 μRNase/ml, 250 propidium iodide/ml, and 1202 CountBright™ Absolute Count Bead/50 μl As shown in Table V below, the information collected in this analysis includes but is not limited to: absolute and relative nuclei counts, which were observed to become reduced in a cisplatin concentration-dependent manner; anti-cleaved PARP positive chromatin, which increased in a cisplatin concentration-dependent manner; shift in anti-γH2AX-associated fluorescence, which increased in a cisplatin concentration-dependent manner; anti-phospho-H3 positive nuclei which was reduced in a cisplatin concentration-dependent manner, and other changes to cell cycle, which can be largely described as an accumulation of cells in the G2/M phase of the cell cycle.

TABLE V

Multiplexed Analysis of Nuclei Count, H2AX, H3 and PARP in Response to Cisplatin

| Cisplatin (μg/ml) | % Relative Nuclei Count | γH2AX-associated Shift (Fold Increase)† | Phospho-H3+ Nuclei (Fold Increase)† | Cleaved PARP+ Nuclei (Fold Increase)† | Proportion of Cells in G2M (Fold Increase)† |
|---|---|---|---|---|---|
| 0 | 100 | 1.00 | 1.00 | 1.00 | 1.0 |
| 0.0024 | 111 | 1.01 | 0.91 | 0.92 | 1.3 |
| 0.0049 | 109 | 1.11 | 1.00 | 0.96 | 1.2 |
| 0.0098 | 105 | 1.16 | 0.90 | 0.99 | 1.2 |
| 0.0195 | 102 | 1.23 | 0.90 | 0.99 | 1.3 |
| 0.0391 | 100 | 1.30 | 0.98 | 1.00 | 1.3 |
| 0.0781 | 95 | 1.40 | 0.94 | 1.09 | 1.4 |
| 0.1563 | 91 | 1.52 | 0.80 | 1.26 | 1.7 |
| 0.3125 | 77 | 1.73 | 0.82 | 1.74 | 1.9 |
| 0.625 | 66 | 2.16 | 0.45 | 3.20 | 2.2 |
| 1.25 | 53 | 2.90 | 0.28 | 8.60 | 2.3 |
| 2.5 | 37 | 3.90 | 0.22 | 22.78 | 2.1 |

†Fold Increase is relative to Control

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A kit comprising:
   one or more eukaryotic cell membrane lysis solutions;
   exactly one fluorescent nucleic acid dye; and
   three or more fluorescent nuclei-associated epitope-specific antibodies or ligands (NAESA/L) that bind specifically to distinct nuclei-associated epitopes, wherein the three or more fluorescent NAESA/L have fluorescent emission spectra that do not substantially overlap with one another or with the fluorescent emission spectrum of the NAD.

2. The kit according to claim 1 further comprising one or more of RNase; counting beads; a computer-readable medium comprising instructions for statistical analyses for characterizing in vitro genotoxicity as the result of clastogenicity, aneugenicity, or cytotoxicity based on the behavior of a eukaryotic cell in response to exposure to a chemical or physical agent and following exposure to the kit components.

3. The kit according to claim 1, wherein one of the nuclei-associated epitopes is associated with histone and histone-like proteins, histone modifications, markers of cells in metaphase, markers of apoptosis, markers of DNA damage checkpoints/response, transcription factors, DNA adducts, DNA methylation sites, proteins associated with DNA methylation, proteins associated with histone modification, or markers of cell proliferation.

4. The kit according to claim 1, wherein one, two, or three of the three or more NAESA/L specifically bind to a nuclei-associated epitope associated with a protein selected from the group consisting of histone 1 (H1), histone 2A (H2A), histone 2A.Z (H2A.Z), histone 2AX (H2AX), histone 3 (H3), histone 4 (H4), centromere protein A (CENP-A), centromere protein B (CENP-B), centromere identifier (CID), heterochromatin protein (HP1), phosphorylated gamma histone 2AX (γH2AX), phosphorylated histone H3 (H3), HpTGEKP motif, acetylated-H3, methylated-H3, ubiquinated H2B, cleaved poly(ADP-ribose) polymerase (PARP), cleaved caspase 3, 7, or 9, checkpoint kinase 1 (ChK1), checkpoint kinase 2 (ChK2), ataxia telangiectasia mutated serine-protein kinase (ATM), ataxia telangiectasia protein kinase (ATR), histone 2B (H2B), aryl hydrocarbon receptor (AhR), breast cancer susceptibility protein 1 (BRCA1), breast cancer susceptibility protein 2 (BRCA2), DNA repair protein RAD51 (RAD51), tumor protein p53 (p53), 5-methyl cytidine, 8-hydroxydeoxyguanosine (8-OHdG), Ki-67, proliferating cell nuclear antigen (PCNA), phosphorylated Mitotic Protein, phospho-Ser/Thr-Pro Mitotic protein monoclonal #2 (MPM2), cAMP response element-binding protein (CREB), CREB-binding protein (CBP), NFKB, and aryl hydrocarbon receptor nuclear translocator (ARNT).

5. The kit according to claim 1, wherein one of the three or more NAESA/L specifically binds to a nuclei-associated epitope present on a DNA adduct selected from the group consisting of 0-6-methylguanine, 7-methylguanine, 8-oxo-deoxyguanosine, 1,N(2)-propane deoxyguanosines, and 8-oxo-7,8-dihydro-2'-deoxyguanosine.

6. The kit according to claim 1, one of the three or more NAESA/L specifically binds to a nuclei-associated epitope associated with a DNA methylation site selected from the group consisting of 5-methyl cytidine, 5-carboxylcytosine, 5-formylcyto sine, 5-hydroxymethylcytosine, and 3-methylcytosine.

7. The kit according to claim 1, wherein one of the three or more NAESA/L specifically binds to a nuclei-associated epitope present on DNA methyltransferase 1 (DNMT1), DNA methyltransferase 2 (DNMT2), DNA methyltransferase 3A (DNMT3A), DNA methyltransferase 3B (DNMT3B), DNA methyltransferase 3-like protein (DNMT3L), or methyl 5'-cytosine-phosphate-guanine-3' (CPG-binding proteins.

8. The kit according to claim 1, wherein one of the three or more NAESA/L specifically binds to a nuclei-associated epitope present on phosphorylated Sirtuin 2 (SIRT2).

9. The kit according to claim 1, wherein one of the three or more NAESA/L specifically binds to a nuclei-associated epitope present on a marker of cell proliferation selected from the group consisting of proliferating cell nuclear antigen (PCNA) and Ki-67.

10. A composition in the form of a single reagent solution comprising:
  water;
  one or more cell lysis agents in amounts effective to lyse cells;
  a fluorescent nucleic acid dye (NAD), and
  three or more fluorescent nuclei-associated epitope-specific antibodies or ligands (NAESA/L) that specifically bind to a distinct nuclei-associated epitope of interest, wherein the three or more fluorescent NAESA/L have fluorescent emission spectra that do not substantially overlap with one another or with the fluorescent emission spectrum of the NAD;
  wherein, in said reagent solution prior to exposure to cells, the fluorescent NAD is unassociated with chromatin and each of the three or more fluorescent NAESA/L is unassociated with the nuclei-associated epitope of interest, and
  wherein said reagent solution, upon exposure to cells, causes cell lysis, nucleic acid labeling, and labeling of three or more distinct nuclei-associated epitopes by the three or more NAESA/L.

11. The composition according to claim 10, wherein the one or more cell lysis agents comprise a combination of NaCl, sodium citrate, and octylphenyl-polyethylene glycol.

12. The composition according to claim 10, wherein the NAD is a DNA-specific dye.

13. The composition according to claim 10, wherein the NAD is not a DNA-specific dye, and the composition further comprises RNase A.

14. The composition according to claim 10 further comprising counting beads.

15. The composition according to claim 10, wherein not more than one NAD is present in the reagent composition.

16. The composition according to claim 10, wherein one, two, or three of the three or more NAESA/L specifically binds to a nuclei-associated epitope associated with a protein selected from the group consisting of histone 1 (H1), histone 2A (H2A), histone 2A.Z (H2A.Z), histone 2AX (H2AX), histone 3 (H3), histone 4 (H4), centromere protein A (CENP-A), centromere protein B (CENP-B), centromere identifier (CID), heterochromatin protein (HP1), phosphorylated gamma histone 2AX (γH2AX), phosphorylated histone H3 (H3), HpTGEKP motif, acetylated-H3, methylated-H3, ubiquinated H2B, cleaved poly(ADP-ribose) polymerase (PARP), cleaved caspase 3, 7, or 9, checkpoint kinase 1 (ChK1), checkpoint kinase 2 (ChK2), ataxia telangiectasia mutated serine-protein kinase (ATM), ataxia telangiectasia protein kinase (ATR), histone 2B (H2B), aryl hydrocarbon receptor (AhR), breast cancer susceptibility protein 1 (BRCA1), breast cancer susceptibility protein 2 (BRCA2), DNA repair protein RAD51 (RAD51), tumor protein p53 (p53), 5-methyl cytidine, 8-hydroxydeoxyguanosine (8-OHdG), Ki-67, proliferating cell nuclear antigen (PCNA), phosphorylated Mitotic Protein, phospho-Ser/Thr-Pro Mitotic protein monoclonal #2 (MPM2), cAMP response element-binding protein (CREB), CREB-binding protein (CBP), NFKB, and aryl hydrocarbon receptor nuclear translocator (ARNT).

17. The composition according to claim 10, wherein the NAD is not a DNA-specific dye, three fluorescent NAESA/L that specifically bind to distinct nuclei-associated epitopes of interest are present, and the composition further comprises RNase A and counting beads.

18. The composition according to claim 17, wherein
  the NAD is present at a concentration of about 0.1 µg/ml to about 15 µg/ml,
  the RNase A is present at a concentration of about 0.05 mg/ml to about 5.0 mg/ml,
  each of the three NAESA/L is present in an amount of about 0.5 µl/ml to about 5 µl/ml, and
  counting beads are present at a concentration of about 500 beads/ml to about 50,000 beads/ml.

19. The composition according to claim 10, wherein the single reagent solution does not contain cellular debris.

20. The composition according to claim 10, wherein the single reagent solution consists essentially of an aqueous saline solution containing the one or more cell lysis agents, the fluorescent NAD, the three of more NAESA/L, and optionally one or more of RNase A, counting beads, and an additional fluorescent or luminescent reagent selected from the group of a mitochondrial membrane potential dye and luciferase/luciferin.

* * * * *